US012075830B2

(12) United States Patent
Van Lancker et al.

(10) Patent No.: US 12,075,830 B2
(45) Date of Patent: Sep. 3, 2024

(54) AEROSOL-GENERATING DEVICE WITH PLANAR HEATER

(71) Applicant: Philip Morris Products S.A., Neuchatel (CH)

(72) Inventors: Pieter Van Lancker, Kortrijk (BE); Louis-Philippe Vancraeynest, Kortrijk (BE); Simon Desnerck, Kortrijk (BE)

(73) Assignee: Philip Morris Products S.A., Neuchatel (CH)

( * ) Notice: Subject to any disclaimer, the term of this patent is extended or adjusted under 35 U.S.C. 154(b) by 910 days.

(21) Appl. No.: 16/973,550

(22) PCT Filed: Jun. 13, 2019

(86) PCT No.: PCT/EP2019/065486
§ 371 (c)(1),
(2) Date: Dec. 9, 2020

(87) PCT Pub. No.: WO2019/238819
PCT Pub. Date: Dec. 19, 2019

(65) Prior Publication Data
US 2021/0251289 A1     Aug. 19, 2021

(30) Foreign Application Priority Data

Jun. 14, 2018 (EP) .................................. 18177759

(51) Int. Cl.
*A24F 40/46* (2020.01)
*A24F 40/70* (2020.01)
(Continued)

(52) U.S. Cl.
CPC .............. *A24F 40/46* (2020.01); *A24F 40/70* (2020.01); *A24D 1/20* (2020.01); *A24F 40/20* (2020.01); *A24F 40/50* (2020.01)

(58) Field of Classification Search
CPC .......... A24F 40/46; A24F 40/70; A24F 40/20; A24F 40/50; A24F 1/20
(Continued)

(56) References Cited

U.S. PATENT DOCUMENTS 4,819,665 A * 4/1989 Roberts .................... A24D 1/22
131/194
4,917,119 A * 4/1990 Potter .................... A24F 42/10
131/194

(Continued)

FOREIGN PATENT DOCUMENTS

CN     104768407 A     7/2015
CN     106535680 A     3/2017
(Continued)

OTHER PUBLICATIONS

International Search Report and Written Opinion issued Sep. 11, 2019 in PCT/EP2019/065486 filed Jun. 13, 2019.
(Continued)

*Primary Examiner* — Harshad C Patel
(74) *Attorney, Agent, or Firm* — Oblon, McClelland, Maier & Neustadt, L.L.P.

(57) ABSTRACT

An aerosol-generating device for generating an inhalable aerosol is provided, the aerosol-generating device including: a heating chamber configured to receive a planar aerosol-generating article containing an aerosol-generating substrate; and a heating element having an essentially planar shape and being configured to heat the planar aerosol-generating article, at least a heating surface of the heating element including a surface structure configured to enable lateral airflow between the heating surface and the planar aerosol-generating article after insertion of the planar aerosol-generating article into the heating chamber. A method for
(Continued)

Figure 1:
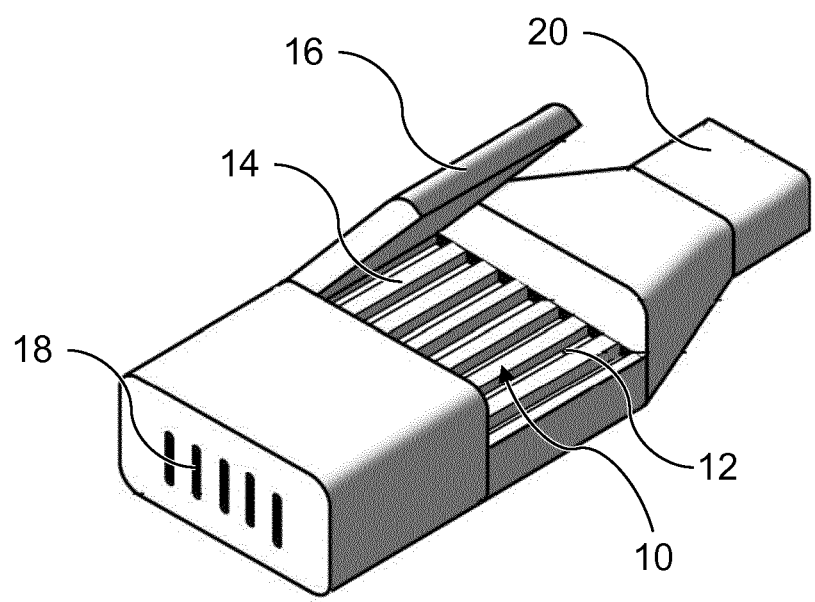

manufacturing an aerosol-generating device for generating an inhalable aerosol is also provided.

16 Claims, 7 Drawing Sheets

(51) Int. Cl.
  *A24D 1/20*   (2020.01)
  *A24F 40/20*   (2020.01)
  *A24F 40/50*   (2020.01)
(58) Field of Classification Search
  USPC .......................................................... 131/329
  See application file for complete search history.

(56) References Cited

U.S. PATENT DOCUMENTS

| | | | | |
|---|---|---|---|---|
| 5,179,966 | A * | 1/1993 | Losee | A24F 40/46 131/194 |
| 5,322,075 | A * | 6/1994 | Deevi | A24F 40/46 131/194 |
| 7,540,286 | B2 * | 6/2009 | Cross | A61M 16/1075 128/203.26 |
| 7,834,295 | B2 * | 11/2010 | Sharma | F42B 3/124 123/143 R |
| 8,333,197 | B2 * | 12/2012 | Cross | A61M 15/008 128/200.14 |
| 10,368,580 | B2 * | 8/2019 | Rostami | A24F 40/30 |
| 11,083,856 | B2 * | 8/2021 | Buchberger | A24F 40/485 |
| 11,717,479 | B2 * | 8/2023 | Cassella | A61K 31/5517 424/489 |
| 11,744,964 | B2 * | 9/2023 | Fraser | A61M 11/042 392/386 |
| 11,752,284 | B2 * | 9/2023 | Dickens | H05B 1/0297 131/328 |
| 2005/0037506 | A1 * | 2/2005 | Hale | A61M 11/001 436/157 |
| 2005/0268911 | A1 | 12/2005 | Cross et al. | |
| 2009/0235926 | A1 | 9/2009 | Cross et al. | |
| 2011/0233043 | A1 | 9/2011 | Cross et al. | |
| 2013/0180525 | A1 | 7/2013 | Cross et al. | |
| 2016/0120221 | A1 | 5/2016 | Mironov et al. | |
| 2017/0095623 | A1 | 4/2017 | Trzecieski | |
| 2017/0105246 | A1 | 4/2017 | Cross et al. | |
| 2017/0164657 | A1 | 6/2017 | Batista | |
| 2017/0311647 | A1 | 11/2017 | Batista et al. | |
| 2017/0347715 | A1 | 12/2017 | Mironov et al. | |

FOREIGN PATENT DOCUMENTS

| | | |
|---|---|---|
| CN | 107427086 A | 12/2017 |
| EP | 2 991 516 | 3/2016 |
| JP | 2015-532828 A | 11/2015 |
| KR | 10-2015-0047616 A | 5/2015 |
| KR | 10-2017-0020782 A | 2/2017 |
| RU | 2 602 969 C2 | 2/2016 |
| WO | WO 2015/177046 A1 | 11/2015 |
| WO | WO 2016/005533 A1 | 1/2016 |
| WO | WO 2017/182249 A1 | 10/2017 |
| WO | WO 2017/202965 A1 | 11/2017 |

OTHER PUBLICATIONS

Russian Search Report issued Jul. 16, 2021 in Russian Patent Application No. 2021100159 (submitting English translation only), 2 pages.
Combined Chinese Office Action and Search Report issued Mar. 21, 2023 in Chinese Patent Application No. 201980034429.3 (with English translation), 15 pages.
Office Action issued Jan. 26, 2022 in corresponding Japanese Patent Application No. 2020-568795 (English Translation only), 5 pages.
Combined Chinese Office Action and Search Report issued on Oct. 10, 2023 in Chinese Patent Application No. 201980034429.3 (with unedited computer-generated English translation), 13 pages.
Korean Office Action issued on Nov. 15, 2023 in Korean Patent Application No. 10-2020-7034519 (with unedited computer-generated English translation), 8 pages.
European Office Action mailed on Apr. 20, 2024, issued in European Patent Application No. 19 731 235.8 filed on Jun. 13, 2019, total 11 pages (citing document 1, therein).
Korean Notice of Allowance mailed on May 9, 2024, issued in Korean Patent Application 10-2020-7034519 filed on Jun. 13, 2019, with English Translation, total 5 pages, citing document 15 therein.

* cited by examiner

AEROSOL-GENERATING DEVICE WITH PLANAR HEATER

The invention relates to an aerosol-generating device for generating an inhalable aerosol. Aerosol-generating devices are known which heat but not burn aerosol-generating substrate such as tobacco. These devices heat aerosol-generating substrate to a sufficiently high temperature for creating an aerosol for inhalation by the user.

These aerosol-generating devices typically comprise a heating chamber, wherein a heating element is arranged within the heating chamber. An aerosol-generating article comprising aerosol-generating substrate can be inserted into the heating chamber and heated by the heating element. The heating element is typically configured as a heating blade and penetrates into the aerosol-generating substrate of the aerosol-generating article when the article is inserted into the heating chamber. A heating blade limits the contact surface between the heating element and the aerosol-generating substrate.

Due to this lack of contact surface, the heating element needs to be raised to a higher temperature for heating the aerosol-generating substrate further away from the heating element so that this substrate also creates the desired aerosol.

Furthermore, once the substrate close to the heating element has released the desired aerosol, the dry substrate becomes worse in transferring heat to the substrate further away from the heating element. Thus, the heating element also needs to be raised to a higher temperature for heating the further substrate to the desired temperature. This may result in overheating, thereby releasing unwanted flavors.

Consequently, there is a need for an aerosol-generating device with optimized heating of aerosol-generating substrate contained in aerosol generating articles.

For solving this and further objects, the present invention proposes an aerosol-generating device for generating an inhalable aerosol. The device comprises a heating chamber configured to receive a planar aerosol-generating article containing aerosol-generating substrate and a heating element. The heating element has an essentially planar shape and is configured to heat a planar aerosol-generating article. At least a heating surface of the heating element comprises a surface structure which is configured for enabling lateral airflow between the heating surface and a planar aerosol-generating article after insertion of the planar aerosol-generating article into the heating chamber.

Conventional aerosol-generating articles have a cylindrical shape resembling traditional cigarettes. The aerosol-generating articles used with the aerosol-generating device according to the present invention are planar. A planar shape means that the articles have two planar sides being arranged opposite to each other, while side surfaces have a small surface area in comparison to the surface area of the planar sides. The thickness of the articles measured as the distance between the planar sides is small in comparison to be length of the articles. The length and width of the articles is at least 3 times, preferably 5 times, more preferably 7 times larger than the thickness of the articles. The heating element of the aerosol-generating device has a planar shape corresponding to the aerosol-generating articles. A planar shape of the heating element means that the heating element is configured to heat the planar side or both planar sides of the aerosol-generating article. The corresponding heating surface of the heating element is thus planar including surface structures as described in more detail below. The part of the heating element facing away from the article, that means the part of the heating element opposite the heating surface, may not be planar. This part may comprise elements such as contacts.

By means of the planar heating element, a uniform heating of the aerosol-generating substrate contained in the aerosol-generating articles can be achieved. Consequently, uniform aerosol generation can be achieved. Also, it is not necessary to heat the heating element to the temperature higher than the temperature required for releasing an aerosol from the aerosol-generating substrate. Hence, a power supply such as a battery provided for operating the heater may be provided smaller and/or with a lower capacity for generating the same amount of aerosol.

The surface structure may be configured as channels in the surface of the heating element facing the article, when the article is inserted into the heating chamber. These channels may particularly be beneficial if the heating element comes into direct contact with the article. In this case, air may still flow through the channels next to the article and between the heating element and the article. The channels may be arranged on the surface of the heating element such that air may be drawn from ambient atmosphere towards and between the article and the heating element and further towards a mouth of a user. The surface structure is arranged such that a lateral airflow is enabled between the heating surface of the heating element and the inserted article. In other words, the air flows between the planar surfaces of the heating element and the aerosol-generating article. The volatile components of the aerosol-generating substrate generated by operation of the heating element may thus optimally be entrained by the air flow. The lateral air flow direction is preferably parallel to the longitudinal axis of the device in the planar plane of the heating surface of the heating element and the planer plane of the side of the aerosol-generating article.

The surface structure may alternatively be configured as curved channels or channels with a zigzag shape. The channels may comprise multiple branches, wherein a single channel may split into multiple branches, or wherein multiple branches may join to form a single channel. The channels may have a shape to increase the time air takes for passing between the heating element and the article. Aerosol generation may in this way be optimized. The surface structure may be configured as protrusions or grooves or dents in the heating element. The surface structure may be configured as a rough surface texture. An optically appealing shape such as a logo, text or artwork may be presented in the surface of the heating element as the surface structure enabling airflow between the heating element and the article. The surface structure may be defined by hard edges or by smooth transitions. Smooth transitions may have the benefit of preventing dirt or aerosol deposits on the surface structure. Also, the surface structure may be easy to clean by a user by means of a tool such as a brush, if the surface structure is defined by smooth transitions.

The heating element may be configured to heat a single planar side or both planar sides of a planar aerosol-generating article.

Heating a single side of a planar aerosol-generating article may have the advantage that the heating element only has to be provided on a single side of the aerosol-generating article. Heating the article on both sides has the advantage that a more uniform aerosol generation may be achieved.

The heating element may be configured to be spaced apart from or contact or clamp a planar aerosol-generating article after insertion of the planar aerosol-generating article into the heating chamber.

The heating chamber may be defined by the space between two planar heating surfaces of the heating element. The heating surfaces are preferably arranged opposite each other and facing each other.

Providing the heating element spaced apart from the aerosol-generating article has the advantage that the article can be easily inserted into the heating chamber. This embodiment is particularly useful if the heating element is configured adjacent to both sides of the article and for heating both sides of the article. A direct contact between the heating element and the article may optimize heat transfer from the heating element towards the aerosol-generating substrate contained in the aerosol-generating article. Clamping the article between the heating element facilitates secure holding of the article in the heating chamber inside of the heating element.

The heating element may comprise multiple separately controllable sections for heating different sections of a planar aerosol-generating article.

This embodiment may utilize a heating element which heats a single planar side of the article or both planar sides of the article. In any case, different sections of the aerosol-generating substrate contained in the article are subsequently heated by the separately controllable sections of the heating element. A different section of the substrate may be heated each time the user puffs on the aerosol-generating device or after depletion of a section of substrate.

The heating element may comprise at least a separately controllable section for preheating at least a section of a planar aerosol-generating article, wherein the heating element may comprise at least a separately controllable section for heating at least a preheated section of a planar aerosol-generating article for generating an aerosol.

In this embodiment, a section of the heating element is provided for preheating the substrate, while a further section of the heating element is provided for finally releasing the aerosol. The response time of the aerosol-generating device for releasing aerosol can thus be reduced. Preferably, the first section of the heating element for preheating the substrate contained in the article is provided covering a first planar side of the article. The second section for releasing the aerosol is provided on the second planar side of the article opposite the first side. When release of aerosol is desired, the second section is heated, while the first section for preheating is heated independently of the release of aerosol. The second section for releasing aerosol may comprise multiple independently controllable sections such that sections of the substrate contained in the article may be heated to a degree that aerosol is released, while the other sections of the substrate are only preheated by the first section of the heating element. Pairs of sections of the heating element for preheating and final heating may be provided and arranged opposite each other on both sides of inserted articles.

The heating element may comprise a slit or hinge or a flexible section for enabling insertion of a planar aerosol-generating article into the heating chamber.

The heating element may comprise two separate heating sections, the first heating section being arranged adjacent to a first planar side of the article, while the second heating section is arranged adjacent to the second planar side of the article. The two heating sections of the heating element may form a slit for inserting the article. Alternatively, the heating sections of the heating element may be connected with each other by a hinge so that the heating sections can be opened for insertion of the article and closed after insertion of the article. As a further alternative, a section of the heating element, preferably the section connecting the two heating sections of the heating element, is configured flexible such that the heating sections of the heating element can be bent outwards for enabling insertion of the article. After insertion of the article, the heating sections of the heating element are closed again such that the article is arranged between the heating sections of the heating element. The flexible section of the heating element preferably is configured elastic such that the heating sections of the heating element automatically return to their initial position after insertion of the article between the heating sections.

At least a section of the heating element may have a heating surface larger or smaller than a planar aerosol-generating article.

Configuring the heating element larger than the article enables preheating of air before the air is reaching the article. Also, articles with different dimensions may be used with a single heating element. Configuring the heating element smaller than the article enables heating of different sections of the article during different heating operations. Only a section of the article may be heated during a first heating operation, while a different section of the article may be heated in a further heating operation. Also, parts of the article may have a different functionality such as being configured as a tap for holding the article. This part of the article may not be covered by the heating element.

The heating element may be configured movable towards or away from or relative to a planar aerosol-generating article during operation of the heating element.

The heating element may be configured to move towards the article after the article has been inserted into the heating chamber. The movement may be facilitated by the user manually moving the heating elements or automatically by the device. A movement of the heating element away from the article may facilitate insertion of the article into the heating chamber. Moving of the heating element relative to the article enables heating of different sections of the article. The heating element may be configured to be moved relative to the article during a heating operation. The heating element may be configured to be moved relative to the article between puffs of the user. The movement may be induced by the heater being activated, the user pushing a button or by means of a communication interface of the device communicating with an external device such as a smartphone or smartwatch.

At least a first heating section of the heating element may be configured movable with respect to at least a second heating section of the heating element.

This embodiment is particularly preferred if a first stationary heating section of the heating element is provided for preheating the substrate contained in the article, while a second heating section may be configured movable between different sections of the article for heating different sections of the substrate contained in the article for releasing aerosol. Alternatively, both the stationary heating section as well as the movable heating section are operated together for heating the substrate contained in the article, wherein the movable heating section is moved to a section of fresh substrate after depletion of the heated section of the substrate. Preferably, the stationary section of the heating element is arranged adjacent to one planar side of the planar article, while the moveable section of the heating element is arranged adjacent to the other planar side.

The surface structure may be provided as at least one lateral channel extending from a first side of the heating element facing an air inlet towards a second side of the heating element facing a mouthpiece.

The air inlet may be provided upstream of the heating element. The air inlet may be provided at a distal end of the device. The mouthpiece may be provided downstream of the heating element. The mouthpiece may be provided at a proximal end of the device. The plane of the planar heating element is preferably arranged parallel to the longitudinal axis of the device. The plane of an aerosol-generating article inserted into the heating chamber next to the heating element is preferably arranged parallel to the longitudinal axis of the device. A direction perpendicular to the planar sides of the article or the planer heating surfaces of the heating element is perpendicular to the longitudinal axis of the device.

The heating chamber may be formed between at least two planar heating surfaces of the heating element, wherein the at least two planar heating surfaces may have a surface structure mirroring each other or mirroring each other with an offset or having a complementary structure.

A surface structure on a first heating surface of the heating element mirroring the surface structure on a second heating surface of the heating element may particularly beneficial to securely hold an article between the two heating surfaces. If the surface structures of the heating surfaces are offset with respect to each other, this may facilitate airflow around all or essentially all portions of the aerosol-generating article thereby optimally entraining generated aerosol. Similar effects may be achieved by the two heating surfaces having a complementary structure.

The heating surfaces of the heating element preferably have a planar shape except for the above-described surface structure enabling airflow. This may also be denoted as the heating element having an extensive shape. The heating element may also have a curved, conical, pyramidal, dome or 3-D shape depending upon the specific requirements of the aerosol-generating device. The aerosol generating article may have a corresponding shape.

The heating element is preferably provided as a mesh heating element. However, preferably the heating element does not enable air flow through the heating element. The heating element may also be provided as a resistive heating element, as a conductive heating element, by means of infrared LEDs, as a laser heating element, as a plasma heating element, as a combustion heating element or by means of an exothermic chemical reaction. The heating element is preferably made from metal, metal alloys, ceramics, polymers, composite material, other materials or a combination of materials.

The present invention also relates to an aerosol-generating device as described above and a planar aerosol-generating article.

The present invention also relates to a method for manufacturing an aerosol-generating device for generating an inhalable aerosol, the method comprising the following steps:
  i) providing a heating chamber configured to receive a planar aerosol-generating article containing aerosol-generating substrate; and
  ii) providing a heating element, wherein the heating element has an essentially planar shape and is configured to heat a planar aerosol-generating article.

Figure 2:
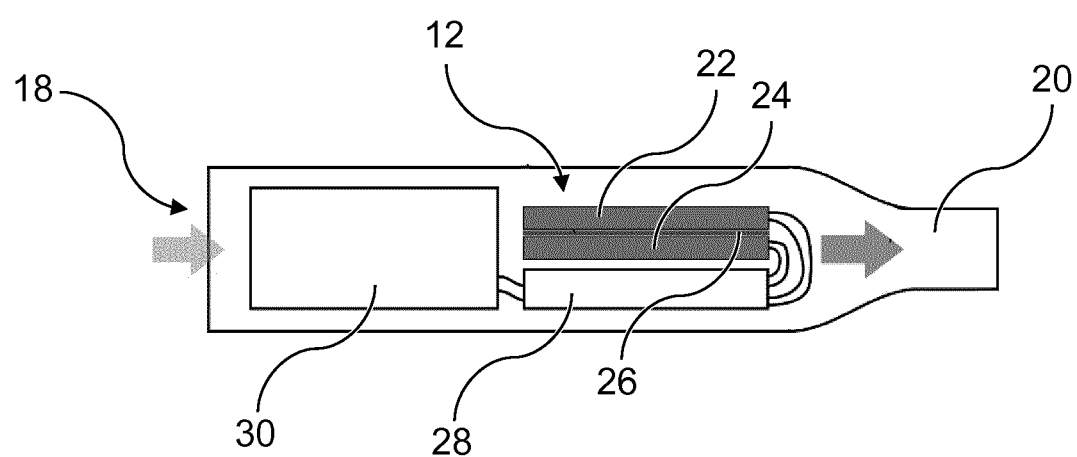
Figure 3:
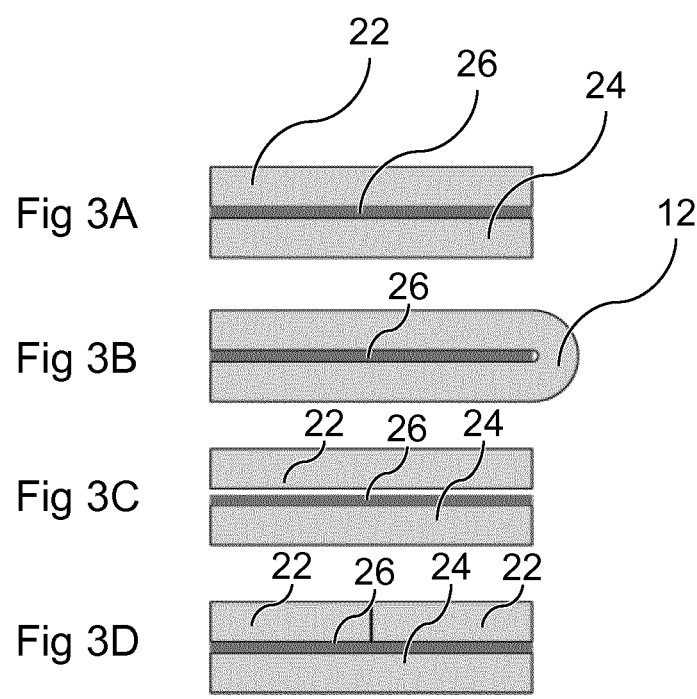
Figure 4:
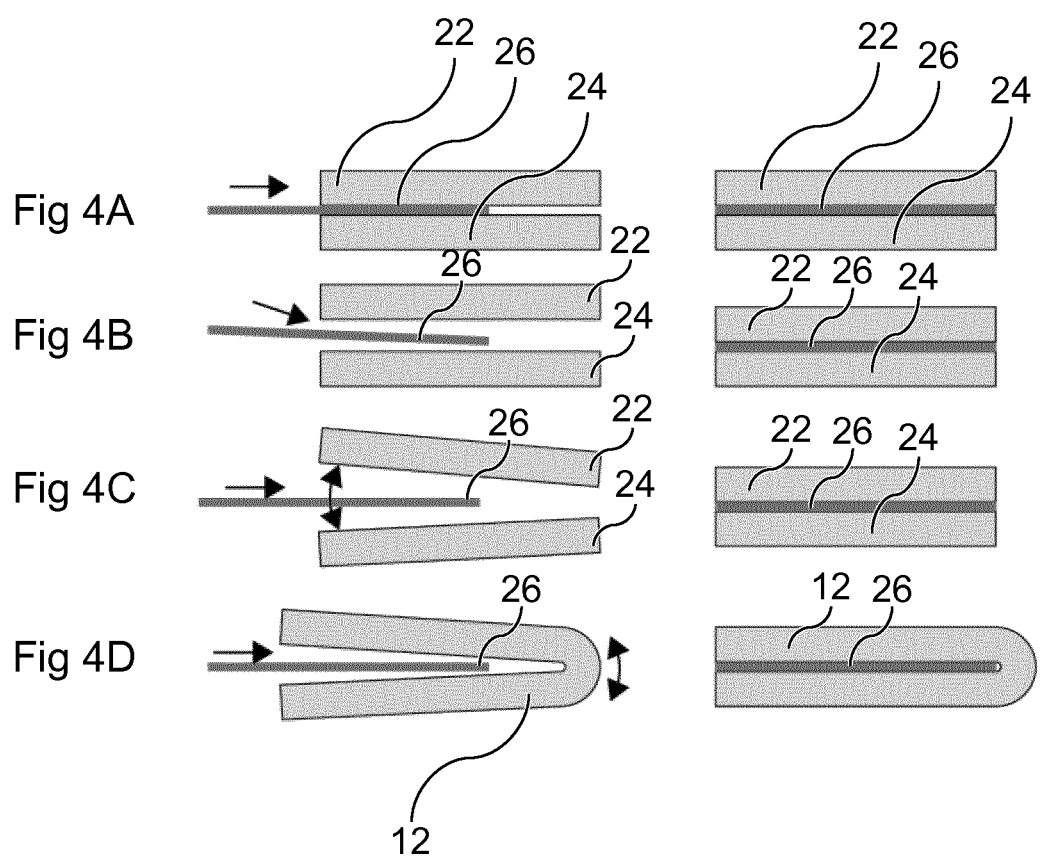
Figure 5:
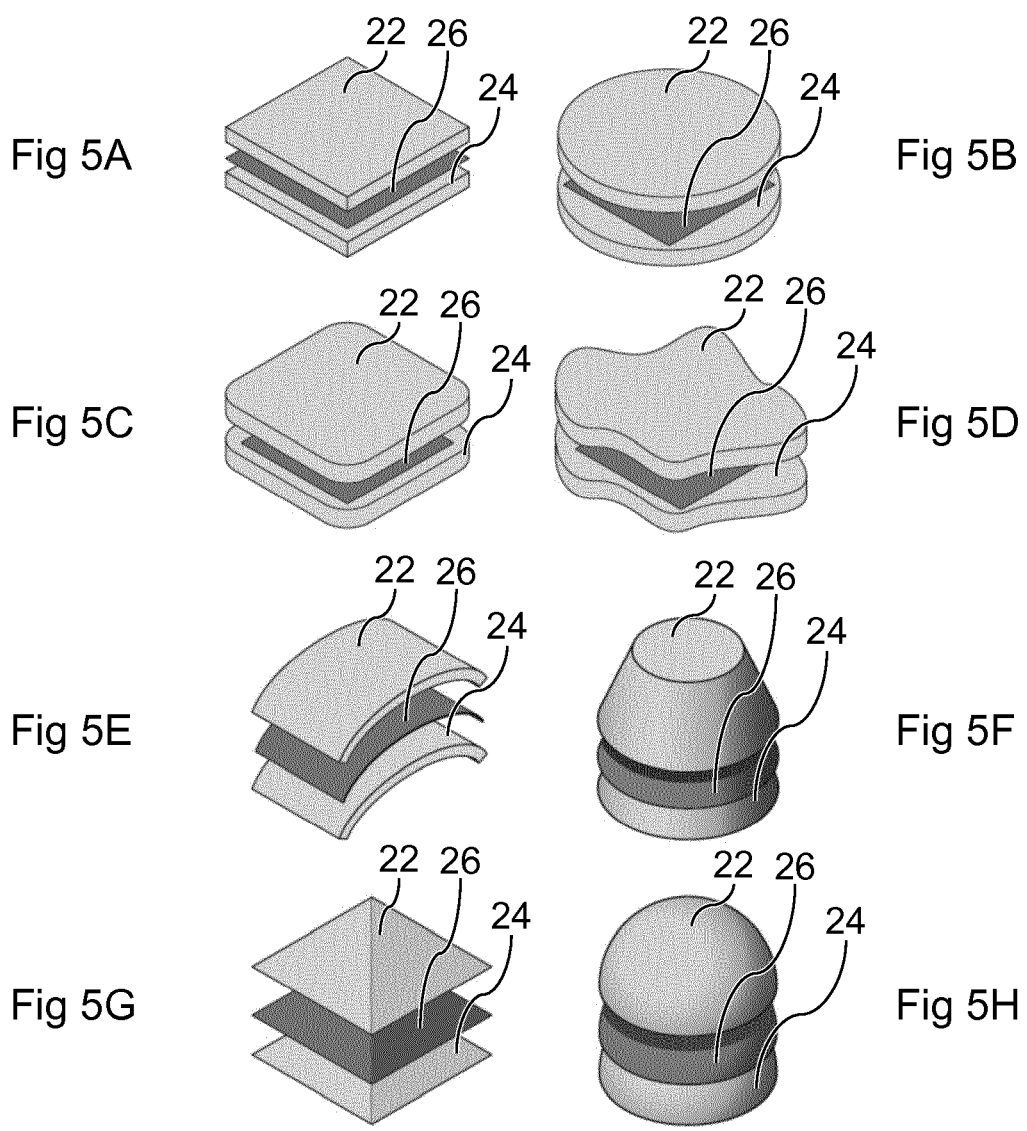
Figure 6:
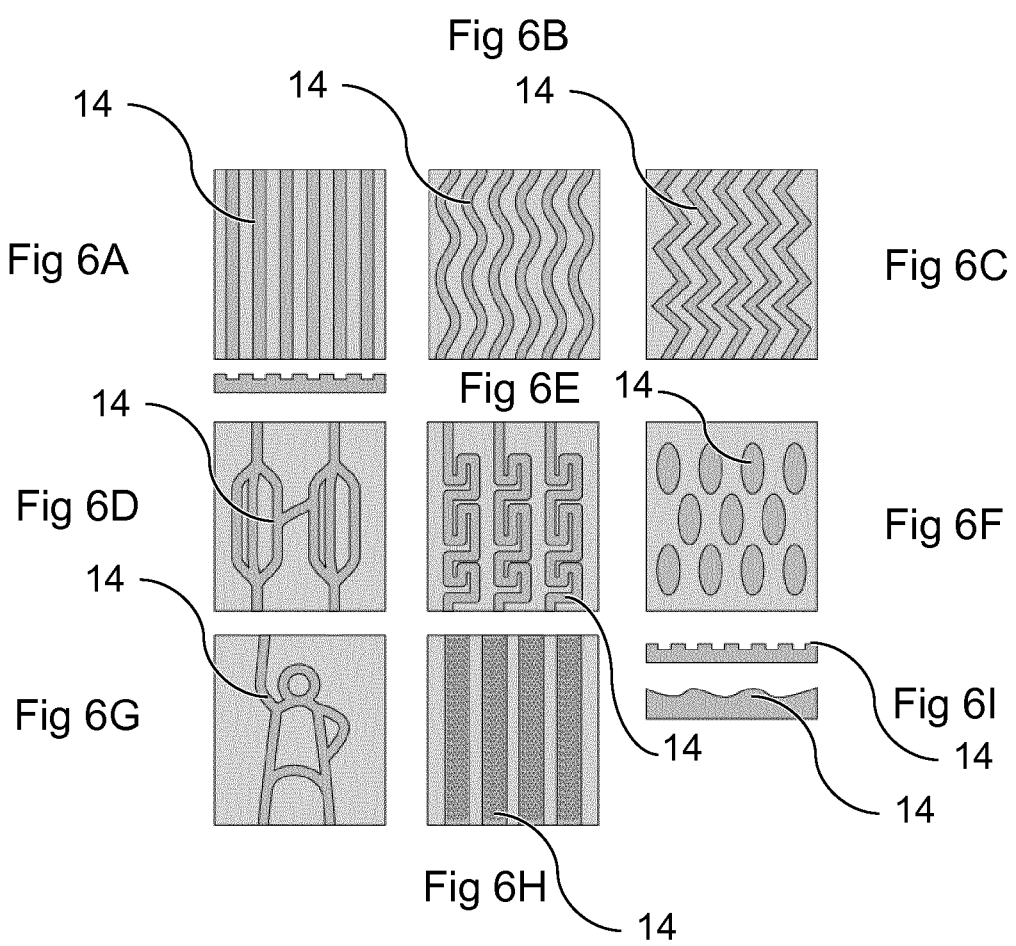
Figure 7:
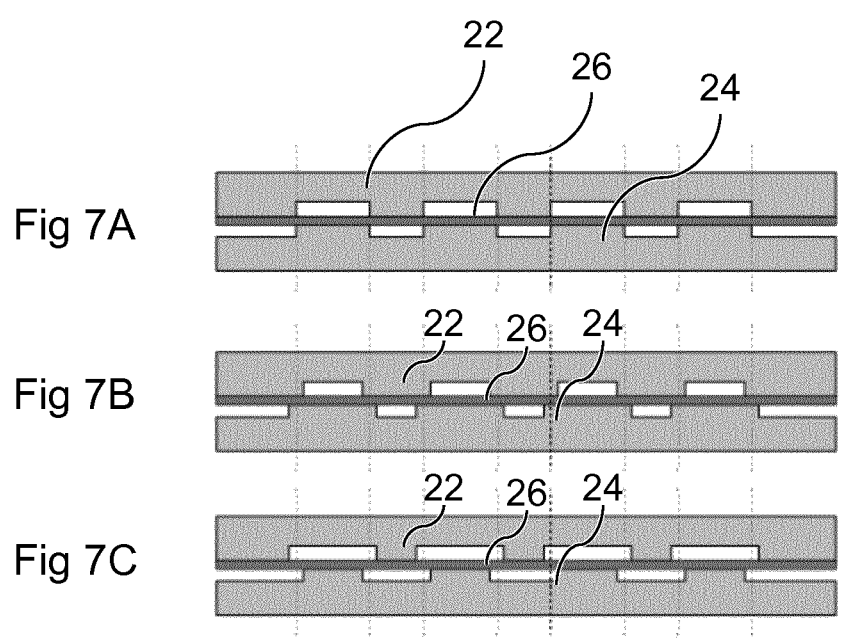

The invention will be described in more detail in the following with reference to the accompanying drawings, which show in:

FIG. 1: an aerosol-generating device according to the present invention;

FIG. 2: a cross sectional view of the aerosol-generating device;

FIG. 3: embodiments of a heating element of the aerosol-generating device;

FIG. 4: further embodiments of the heating element;

FIG. 5: further embodiments of the heating element;

FIG. 6: embodiments of a surface structure in a heating surface of the heating element; and FIG. 7: configurations of the surface structure in a first heating surface and a second heating surface.

FIG. 1 shows an aerosol-generating device according to the present invention. FIG. 1 shows a heating chamber 10 of the device. Within the heating chamber 10, a heating element 12 is arranged. The heating element 12 comprises a surface structure 14 which constitutes channels within the heating surface of the heating element 12 for enabling airflow.

The embodiment shown in FIG. 1 further shows a lid 16 of the device, which can be opened or closed to enable access to the heating chamber 10. The lid 16 may comprise a further heating surface of the heating element 12 of the device. An aerosol-generating article may be inserted between the heating element 12 and the lid 16. After insertion of the article, the lid 16 may be closed to sandwich the aerosol-generating article between the lid 16 and the heating element 12. When the lid 16 comprises a further heating surface of the heating element 12, the aerosol-generating article is then sandwiched between the two heating surfaces of the heating element 12.

The surface structure 14 provided at least on one of the heating surfaces of the heating element 12 enables airflow from air inlets 18 towards a mouthpiece 20 of the device. While the aerosol-generating article is sandwiched between the lid and the lower part of the heating element 12, the channels provided by the surface structure 14 enable airflow between the heating element 12 and the aerosol-generating article. The airflow may optimally entrain the aerosol that is generated by the heating element 12 heating aerosol-generating substrate in the aerosol-generating article.

FIG. 2 shows a cross-sectional view of the aerosol-generating device. As can be seen in FIG. 2, the heating element 12 preferably comprises a first heating element 22 and a second heating element 24. The heating elements 22, 24 have heating surfaces. The first heating element 22 may be positioned above an aerosol-generating article 26 and the second heating element 24 may be arranged below an aerosol-generating article 26, after the aerosol-generating article 26 has been inserted into the heating chamber 10 of the device. The aerosol-generating article 26 is sandwiched between the two heating elements 22, 24.

The aerosol-generating device may comprise a controller 28 and a power supply 30 in the form of a battery. The controller 28 may be configured to control the supply of electrical power from the power supply 30 towards the heating element 12. The controller 28 may comprise a first controller for controlling supply of electrical power from the power supply 30 towards the first heating element 22 and a second controller for controlling supply of electrical power from the power supply 30 towards the second heating element 24. Thus, the controller 28 may be configured to separately control operation of the two heating elements 22, 24. The arrows depicted in FIG. 2 show the airflow from the air inlets 18 towards the mouthpiece 20. If more than two heating elements are provided, the controller may be configured to separately control the operation of these heating elements.

FIG. 3 shows embodiments of the heating element. In the first embodiment shown in FIG. 3A, the first heating element 22 is arranged separately from the second heating element 24, while the aerosol-generating article 26 is positioned in direct contact with the heating surface of the first heating element 22 as well as the heating surface of the second heating element 24.

In FIG. 3B, the heating element 12 is provided as a single heating element. In this embodiment, the section of the heating element 12 connecting the upper portion of the heating element 12 with the lower portion may be configured flexible and elastic such that the heating element 12 may be bent outwards for enabling the aerosol-generating article 26 to be inserted between the sections of the heating element 12.

In FIG. 3C, the first heating element 22 is positioned distanced from the aerosol-generating article 26 thereby simplifying the insertion of the aerosol-generating article 26 into the space between the heating elements 22, 24. In all embodiments, the space between the heating elements 22, 24 preferably defines the heating chamber 10.

In FIG. 3B, the first heating element 22 is configured as multiple independently controllable sections of the heating element 12. In this embodiment, preferably the second heating element 24 arranged below the aerosol-generating article 26 is configured for preheating the aerosol-generating substrate contained in the aerosol-generating article 26. The first heating element 22 arranged above the aerosol-generating article 26 is configured as multiple sections, which are individually heatable. In this embodiment, different portions of the aerosol-generating substrate and the aerosol-generating article 26 can be heated. For example, during each puff of the user, a different portion of the substrate is heated for generating an inhalable vapor. In all embodiments, one of the heating elements 22, 24 may be configured for preheating, while the other heating element 22, 24 may be configured for final heating for generating an inhalable vapor. Also in all embodiments, each of the heating elements 22, 24 may comprises multiple independently operable and controllable heating sections.

FIG. 4 shows the insertion of the aerosol-generating article 26 into the heating chamber 10 between the two heating elements 22, 24. In FIG. 4A, the aerosol-generating article 26 is directly inserted between the heating elements 22, 24. In FIG. 4B, the heating elements 22, 24 are positioned further spaced apart during insertion of the aerosol-generating article 26. After the insertion of the aerosol-generating article 26, the heating elements 22, 24 are moved closer together so as to contact the aerosol-generating article 26 for aerosol generation. FIG. 4C shows an embodiment in which the heating elements 22, 24 are moved apart from each other in a non-uniform manner for facilitating insertion of the aerosol-generating article 26. FIG. 4D shows an embodiment in which a section of the heating element is configured flexible and elastic such that the heating element 12 can be bent to enable insertion of the aerosol-generating article 26.

FIG. 5 shows different shapes of the heating element 12. The preferred shape is shown in FIG. 5A, in which the heating element has a rectangular shape. However, a round shape as shown in FIG. 5B, a shape with curved edges as shown in FIG. 5C, a non-uniform shape as shown in FIG. 5D, a curved shape as shown in FIG. 5A, a cone shape as shown in FIG. 5F, a pyramidal shape as shown in FIG. 5G and a hemispherical shape as shown in FIG. 5H are also possible embodiments.

FIG. 6 shows different embodiments of the surface structure 14 in the heating surface of the heating element 12. The surface structure 14 may be in the shape of straight channels as shown in FIG. 6A, in the shape of curved channels as shown in FIG. 6B, in the form of zigzag channels as shown in FIG. 6C, in the shape of channels splitting into multiple branches and/or multiple branches joining together as shown in FIG. 6D, in the shape such as to prolong the airflow route as shown in FIG. 6E, in the shape of protrusions or dents as shown in FIG. 6F, in the shape of an artwork as shown in FIG. 6G, in the shape of a roughened surface as shown in FIG. 6H or in the shape of hard or smooth transitions as shown in FIG. 6I. The surface structure 14 does not prevent the heating element 12 from having a planar shape and the heating element 12 is considered planar as long as the heating element 12 has an extensive shape and is configured for heating planar aerosol-generating articles 26.

FIG. 7 shows embodiments of the surface structure 14 provided on a heating surface of the first heating element 22 and a second heating element 24 respectively facing the aerosol-generating article 26. FIG. 7A shows surface structures 14 in the heating surfaces of the first heating element 22 and the second heating element 24 which are of complementary shape. This may facilitate optimal entrainment of the aerosol generated in the aerosol-generating article during heating by the heating element 12. FIG. 7B shows an embodiment in which the aerosol-generating article 26 is securely held between the first heating element 22 and the second heating element 24 due to the channels formed by the respective surface structures 14 being smaller. The surface area of the surface contacting the aerosol-generating article is in this embodiment larger than the surface of the channels. FIG. 7C shows an embodiment in which the channels formed in the surface structures of the first heating element 22 and the second heating element 24 are larger so that more air can flow between the aerosol-generating article 26 and the heating elements 22, 24. The surface area of the surface contacting the aerosol-generating article 26 is in this embodiment smaller than the surface of the channels.

The invention claimed is:

1. An aerosol-generating device for generating an inhalable aerosol, the aerosol-generating device comprising:
   a heating chamber configured to receive a planar aerosol-generating article containing an aerosol-generating substrate; and
   a heating element having an essentially planar shape and being configured to heat the planar aerosol-generating article,
   wherein at least a heating surface of the heating element comprises a surface structure configured to enable lateral airflow between the heating surface and the planar aerosol-generating article after insertion of the planar aerosol-generating article into the heating chamber.

2. The aerosol-generating device according to claim 1, wherein the heating element is further configured to heat a single planar side or both planar sides of the planar aerosol-generating article.

3. The aerosol-generating device according to claim 1, wherein the heating element is further configured to be spaced apart from or contact or clamp the planar aerosol-generating article after insertion of the planar aerosol-generating article into the heating chamber.

4. The aerosol-generating device according to claim 1, wherein the heating element comprises multiple separately controllable sections configured to heat different sections of the planar aerosol-generating article.

5. The aerosol-generating device according to claim 1, wherein the heating element comprises at least a separately controllable section configured to preheat at least a section of the planar aerosol-generating article, and wherein the heating element further comprises at least a separately controllable section configured to heat at least the preheated section of the planar aerosol-generating article for generating the inhalable aerosol.

6. The aerosol-generating device according to claim 1, wherein the heating element comprises a slit or hinge or flexible section configured to enable insertion of the planar aerosol-generating article into the heating chamber.

7. The aerosol-generating device according to claim 1, wherein the heating chamber is formed between at least two planar heating surfaces of the heating element.

8. The aerosol-generating device according to claim 1, wherein at least a section of the heating element has a heating surface larger or smaller than the planar aerosol-generating article.

9. The aerosol-generating device according to claim 1, wherein the heating element is configured to be movable towards or away from or relative to the planar aerosol-generating article during operation of the heating element.

10. The aerosol-generating device according to claim 1, wherein at least a first heating section of the heating element is configured to be movable with respect to at least a second heating section of the heating element.

11. The aerosol-generating device according to claim 1, wherein the heating element is configured to be arranged adjacent to both planar sides of the planar aerosol-generating article after insertion of the planar aerosol-generating article into the heating chamber.

12. The aerosol-generating device according to claim 11, wherein the heating element further comprises heating sections on respective sides of the planar aerosol-generating article that are separately controllable.

13. The aerosol-generating device according to claim 1, wherein the surface structure is provided as at least one lateral channel extending from a first side of the heating element facing an air inlet towards a second side of the heating element facing a mouthpiece.

14. The aerosol-generating device according to claim 1,
wherein the heating chamber is formed between at least two planar heating surfaces of the heating element, and
wherein the at least two planar heating surfaces have a surface structure mirroring each other, or mirroring each other with an offset, or having a complementary structure.

15. The aerosol-generating device according to claim 1, further comprising the planar aerosol-generating article.

16. A method for manufacturing an aerosol-generating device for generating an inhalable aerosol, the method comprising the following steps:
i) providing a heating chamber configured to receive a planar aerosol-generating article containing an aerosol-generating substrate; and
ii) providing a heating element having an essentially planar shape and being configured to heat the planar aerosol-generating article,
wherein at least a heating surface of the heating element comprises a surface structure configured to enable lateral airflow between the heating surface and the planar aerosol-generating article after insertion of the planar aerosol-generating article into the heating chamber.

* * * * *